(12) United States Patent
DiGiulio et al.

(10) Patent No.: US 9,856,188 B2
(45) Date of Patent: *Jan. 2, 2018

(54) INTEGRATION OF N-C4/N-C4=/BD SEPARATION SYSTEM FOR ON-PURPOSE BUTADIENE SYNTHESIS

(71) Applicant: UOP LLC, Des Plaines, IL (US)

(72) Inventors: Christopher D. DiGiulio, Chicago, IL (US); John J. Senetar, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/476,627

(22) Filed: Mar. 31, 2017

(65) Prior Publication Data

US 2017/0204025 A1    Jul. 20, 2017

Related U.S. Application Data

(63) Continuation-in-part of application No. 14/749,059, filed on Jun. 24, 2015, now Pat. No. 9,611,192.

(60) Provisional application No. 62/018,973, filed on Jun. 30, 2014.

(51) Int. Cl.
*C07C 5/48* (2006.01)
*C07C 5/327* (2006.01)

(52) U.S. Cl.
CPC ............. *C07C 5/48* (2013.01); *C07C 5/327* (2013.01)

(58) Field of Classification Search
CPC ........... C07C 5/327; C07C 5/48; C07C 11/08; C07C 7/10; C07C 11/167
See application file for complete search history.

(56) References Cited

U.S. PATENT DOCUMENTS 7,414,173 B1 *  8/2008  Herrmann ........ C07K 14/43522
424/93.2

* cited by examiner

*Primary Examiner* — Sharon Pregler

(57) ABSTRACT

A process for the production of butadiene is presented. The process combines the separation of butenes and butadienes extracted from a non-oxidated dehydrogenation process with the separation of butenes and butadienes from an oxidative dehydrogenation process to increase the butadiene yields and reduce the equipment for the recovery of a butadiene product.

17 Claims, 2 Drawing Sheets

INTEGRATION OF N-C4/N-C4=/BD SEPARATION SYSTEM FOR ON-PURPOSE BUTADIENE SYNTHESIS

CROSS REFERENCE TO RELATED APPLICATIONS

This application is a Continuation-in-Part of copending U.S. application Ser. No. 14/749,059 filed Jun. 24, 2015, which application claims priority from U.S. Provisional Application No. 62/018,973 filed Jun. 30, 2014, now expired, the contents of which cited applications are hereby incorporated by reference in their entirety.

FIELD OF THE INVENTION

The present invention relates to a process for the production of butadiene. In particular, this is a process for the integration of a butadiene production process into a petrochemical plant.

BACKGROUND

The use of plastics and rubbers are widespread in today's world. The production of these plastics and rubbers are from the polymerization of monomers which are generally produced from petroleum. The monomers are generated by the breakdown of larger molecules to smaller molecules which can be modified. The monomers are then reacted to generate larger molecules comprising chains of the monomers. An important example of these monomers is light olefins, including ethylene and propylene, which represent a large portion of the worldwide demand in the petrochemical industry. Light olefins, and other monomers, are used in the production of numerous chemical products via polymerization, oligomerization, alkylation and other well-known chemical reactions. Producing large quantities of light olefin material in an economical manner, therefore, is a focus in the petrochemical industry. These monomers are essential building blocks for the modern petrochemical and chemical industries. The main source for these materials in present day refining is the steam cracking of petroleum feeds.

Another important monomer is butadiene. Butadiene is a basic chemical component for the production of a range of synthetic rubbers and polymers, as well as the production of precursor chemicals for the production of other polymers. Examples include homopolymerized products such as polybutadiene rubber (PBR), or copolymerized butadiene with other monomers, such as styrene and acrylonitrile. Butadiene is also used in the production of resins such as acrylonitrile butadiene styrene.

Butadiene is typically recovered as a byproduct from the cracking process, wherein the cracking process produces light olefins such as ethylene and propylene. With the increase in demand for rubbers and polymers having the desired properties of these rubbers, an aim to improving butadiene yields from materials in a petrochemical plant will improve the plant economics.

SUMMARY

The present invention is for the improvement of the recovery of butadienes through a more efficient utilization of equipment in the production process.

A first embodiment of the invention is a process for the recovery of butadiene, comprising passing a first feedstream comprising n-butane to a dehydrogenation unit to generate a first butene process stream comprising n-butene; passing the first n-butene process stream to a butane extraction column to generate a butane overhead stream and a first n-butene stream, wherein the butane extraction column is operated to recover the n-butenes in the first butene stream; passing the first n-butene process stream to a butene extraction column to generate an overhead stream comprising n-butene, and a bottoms stream comprising butadiene passing the overhead stream to an oxydehydrogenation unit to generate a second process stream comprising n-butene and butadiene; passing the second process stream to a butene extraction column to generate an overhead stream comprising n-butene, and a bottoms stream comprising butadiene; passing a feedstream derived from an FCC or an MTO/OTO process to the butane extraction column, to the butene extraction column, or to both columns; and passing the bottoms stream to a butadiene recovery unit to generate a butadiene stream.

A second embodiment of the invention is a process for the recovery of butadiene, comprising, passing a first feedstream comprising n-butane to a dehydrogenation unit to generate a first butene process stream comprising n-butene; passing the first n-butene process stream to a butane extraction column to generate a butane overhead stream and a first n-butene stream, wherein the butane extraction column is operated to recover the n-butenes in the first butene stream; passing the butane overhead stream to a light gas separation unit to generate a vapor phase stream comprising hydrogen, and a liquid phase stream comprising n-butane; passing at least a portion of the stream comprising hydrogen and at least a portion of the liquid phase stream to the dehydrogenation unit; passing the first n-butene process stream to a butene extraction column to generate an overhead stream comprising n-butene, and a bottoms stream comprising butadiene; passing the overhead stream to an oxydehydrogenation unit to generate a second process stream comprising n-butene and butadiene; passing the second process stream to a butene extraction column to generate an overhead stream comprising n-butene, and a bottoms stream comprising butadiene; and passing the bottoms stream to a butadiene recovery unit to generate a butadiene stream.

A third embodiment of the invention is a process for the recovery of butadiene, comprising, passing a first feedstream comprising n-butane to a dehydrogenation unit to generate a first butene process stream comprising n-butene; passing the first n-butene process stream to a butane extraction column to generate a butane overhead stream and a first n-butene stream, wherein the butane extraction column is operated to recover the n-butenes in the first butene stream; passing the first n-butene process stream to a butene extraction column to generate an overhead stream comprising n-butene, and a bottoms stream comprising butadiene; passing the overhead stream to a light gas separation unit to generate a vapor phase stream comprising hydrogen, and a liquid phase stream comprising n-butene; passing at least a portion of the stream comprising hydrogen and at least a portion of the liquid phase stream to an oxydehydrogenation unit; passing a second feedstream comprising n-butene to the oxydehydrogenation unit to generate a second process stream comprising n-butene and butadiene; passing the second process stream to the butene extraction column; and passing the bottoms stream comprising butadiene to a butadiene recovery unit to generate a butadiene stream.

Other objects, advantages and applications of the present invention will become apparent to those skilled in the art from the following detailed description and drawings.

DETAILED DESCRIPTION

The present process solves a problem associated with the heating of butadiene by integrating the extractive solvent system. In the production of butadiene from an on purpose butadiene synthesis process beginning with butane, there is a separation step in between the non-oxidative dehydrogenation of butane to generate butene and the step of oxidative dehydrogenation of butenes to generate butadiene. This is to increase the concentration of butenes to improve the economics of butadiene production. The non-oxidative dehydrogenation also generates some butadienes, and it is less desirable to feed this to the oxidative dehydrogenation step. Therefore, a partial combination of the separation of butadiene step is desirable, removing butadienes from any feed to the oxidative dehydrogenation reactor.

Figure 1:
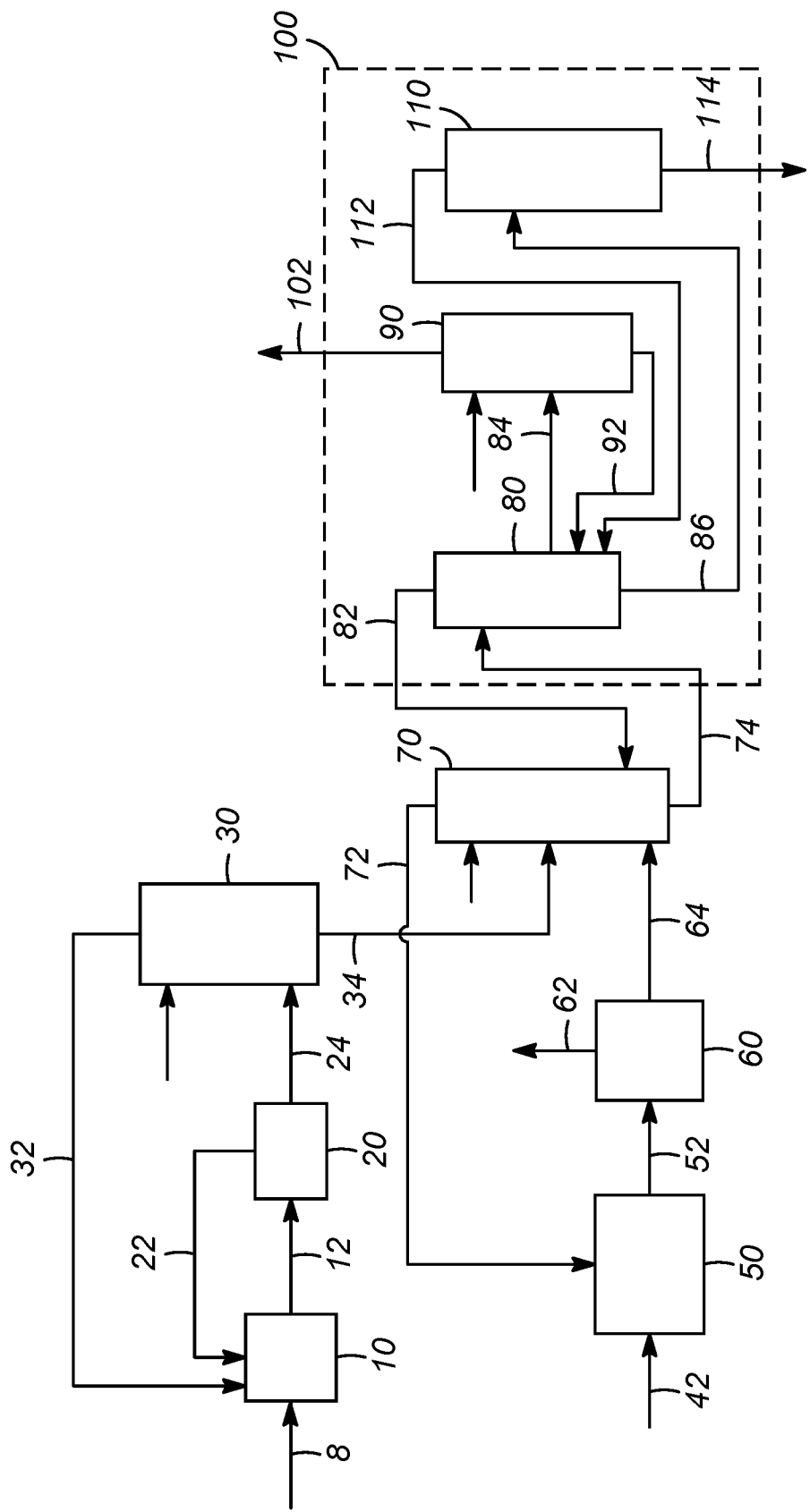
FIG. 1 is the flow scheme of the present invention tying the production of butenes and butadienes together.

In one embodiment, the process can be seen in the FIG. 1, and includes passing a first feedstream 8 to a dehydrogenation unit 10 to generate a first stream 12 comprising n-butene. The first stream 12 can be passed to a first light gas separation unit 20 to generate a vapor phase stream 22 comprising hydrogen, and a first butene stream 24 comprising n-butene. The first butene stream 24 is passed to a butane extraction column 30 to generate a butane overhead stream 32 and a first n-butene stream 34. The amount of n-butane removal would depend on the economics of the extraction step to the overall process. Preferably, the economics provide for the butane extraction column 30 to be operated to remove at least 90% of the n-butanes, and preferably 100%, from the first butene stream. Light gas separation units can comprise a variety of methods for separation of a process stream. One example is a depropanizer, or a fractionation column to separate C3 and lighter components from the process stream, and to have C4 components pass out as a bottoms stream. Other means of separation are known to those skilled in the art, including adsorption-separation systems and the like.

The first feedstream 8 can be a supplied n-butane stream from an outside source, or can be an enriched n-butane stream from a natural gas or other hydrocarbon source. The present invention is not intended to be restricted to such enriched sources of n-butane. In addition, this process can apply to a non-purified feedstream comprising n-butane. The non-purified feedstream can be enriched prior to passage to the dehydrogenation unit 10, or can be passed to the dehydrogenation unit 10 with an added separation process following the dehydrogenation. Light gases are readily removed in the first light gas separation unit 20, and a second separation step can be included to separate C4s from heavier components.

Optionally, the process includes passing a second feedstream 42, comprising n-butene, to an oxydehydrogenation unit 50 to generate an oxydehydro process stream 52 comprising n-butene and butadiene. The oxydehydrogenation unit 50 also includes a source of steam and oxygen. The oxygen can be supplied from an air source. The oxydehydrogenation process stream 52 is passed to a second light gas separation unit 60 to generate a second light gas stream 62, and an intermediate butadiene stream 64. The second light gas stream 62 can comprise CO, CO2, N2 and other components. Purification can be performed with an adsorbent-separation system, or other appropriate separation system. The first n-butene stream 34 and the intermediate butadiene stream 64 are passed to a butene extraction column 70 to generate a butene extraction overhead stream 72 comprising n-butene and a butene extraction bottoms stream 74 comprising butadiene. The butene extraction bottoms 74 is passed to a butadiene recovery unit 100 to generate a butadiene stream 102.

Preferably, the column is operated to recovery substantially all the n-butanes for recycle and to limit the amount of n-butane passed through the process units and reaching the oxydehydrogenation unit 50.

The process can further include passing the butane overhead stream 32 to the dehydrogenation unit 10. The process can further include passing recycling hydrogen by passing the vapor phase stream 22 to the dehydrogenation unit 10.

In one embodiment, the first 20 and second 60 light gas separation units comprise cold-box condensing units. Butanes and butenes have moderate boiling points that are near the freezing point of water. Cooling a gas stream comprising butanes and butenes can be accomplished with a low expense cold-box technology. The gas can be first expanded to cool the gas, then passed through a heat exchanger that cools the expanded gas to a temperature below −15 C. The C4 hydrocarbons then condense while lighter gases such as hydrogen and any carbon oxides remain in the gaseous phase. The cold-box condensing unit 20, 60 is operated at a temperature to sufficiently condense the C4 hydrocarbons. Different C4 hydrocarbons condense at temperatures between 1° C. and −12° C. at one atmosphere. The cold-box unit 20, 60 is preferably operated at a temperature below −15° C. The light gases, including hydrogen, are readily separated from the C4 compounds at these temperatures.

The butane extraction column 30 is a solvent separation process for the separation of olefins from paraffins, or butenes from butane. An appropriate solvent is a solvent comprising a polar nitrogen compound, or a mixture of polar compounds. Examples of solvents, though not limited to these, include n-methylpyrrolidone (NMP), dimethylformamide (DMF), dimethyl acetamide, and acetonitrile (ACN). A common extractive solvent is NMP. The solvent separation process can include additional fractionation units for recovering the solvent and recycling the solvent to the butane extraction column 30.

The butadiene recovery unit 100 can comprise fractionation units and solvent extraction columns. In one embodiment, the butene extraction bottoms 74, comprising butadiene and solvent, is passed to a rectifying column 80 to generate a rectifying overhead stream 82 comprising butene, a rectifying intermediate stream 84 comprising butadiene, and a rectifying bottoms stream 86 comprising solvent. The rectifying bottoms stream 86 is passed to a degassing column 110 to generate a degassing column overhead stream 112 and a bottoms stream 114 comprising recovered solvent for reuse. The degassing column overhead stream 112 is passed to the rectifying column 80. The intermediate stream 84 is passed to a butadiene extraction column 90 to generate a butadiene extraction column bottoms comprising solvent and n-butene, and a butadiene stream 102. The butadiene stream 102 can be further passed to a butadiene purification unit.

The oxydehydrogenation unit 50 includes feeds of stream and an oxygen containing gas, such as air, to the oxydehydrogenation unit. The butene extraction column and the butadiene extraction column are also solvent extraction systems and include the passing of a solvent to the butene extraction column and the butadiene extraction.

In another embodiment, the invention comprises passing a first stream comprising n-butane to a non-oxidative dehydrogenation reactor to generate a second stream comprising n-butane and n-butene, and light gases. The second stream is passed to a light gas separation unit, which cools and compresses the light gases to be separated. The light gases are generated as a vapor phase and comprise hydrogen. The light gas separation unit can utilize cold box technology to condense the C4 hydrocarbons, and generates a third, liquid phase, stream comprising n-butane and n-butene. The third stream is passed to a butane extraction column to generate a fourth stream comprising n-butane and a fifth stream comprising n-butene. The extraction column uses a solvent separation system, with a solvent passed to the extraction column to preferentially absorb the olefin. The fourth stream can be recycled back to the non-oxidative dehydrogenation reactor.

A sixth stream comprising n-butene, along with steam and air, is passed to an oxydehydrogenation reactor to generate a seventh stream comprising butadiene, n-butene and light gases, such as hydrogen. The seventh stream is passed to a light gas separation unit to generate a vapor phase comprising the light gases, and an eighth stream comprising the butadiene and n-butene. The fifth and eighth streams are passed to a butene extraction column at different stages in the column to generate a ninth stream comprising n-butene and a tenth stream comprising butadiene.

The combined butenes from the dehydrogenation reactor and oxydehydrogenation reactor are separated in the butene extraction column and are recycled to the oxydehydrogenation reactor.

The bottoms from the butene extraction column, comprising mostly butadiene and solvent is passed to a butadiene recovery unit. The butadiene recovery unit includes a rectifying column to strip out residual butenes. The rectifying column further generates an intermediate stream comprising butadiene and a bottoms stream comprising solvent. The intermediate stream is passed to a butadiene extraction column to generate a butadiene product stream and a bottoms stream comprising solvent. The bottoms stream from the butadiene extraction column is passed back to the rectifying column.

The bottoms stream from the rectifying column is passed to a degassing column for recovering solvent. The degassing column generates an overhead stream comprising butadiene and is passed back to the rectifying column to be recovered in the butadiene extraction column. The degassing column generates a bottoms stream comprising recovered solvent, which is recycled to the extraction columns for reuse.

In one embodiment, a feedstream which contains hydrocarbons with four carbon atoms where the feedstream is derived from a fluidized catalytic cracking (FCC) process or an oxygenate to olefin (OTO) process such as a methanol to olefin (MTO) process is introduced to the butane extraction column, to the butene extraction column, or to both columns. In one embodiment the feedstream derived from an FCC process is introduced to the butane extraction column. In another embodiment the feedstream derived from an OTO process is introduced into the butene extraction column.

Figure 2:
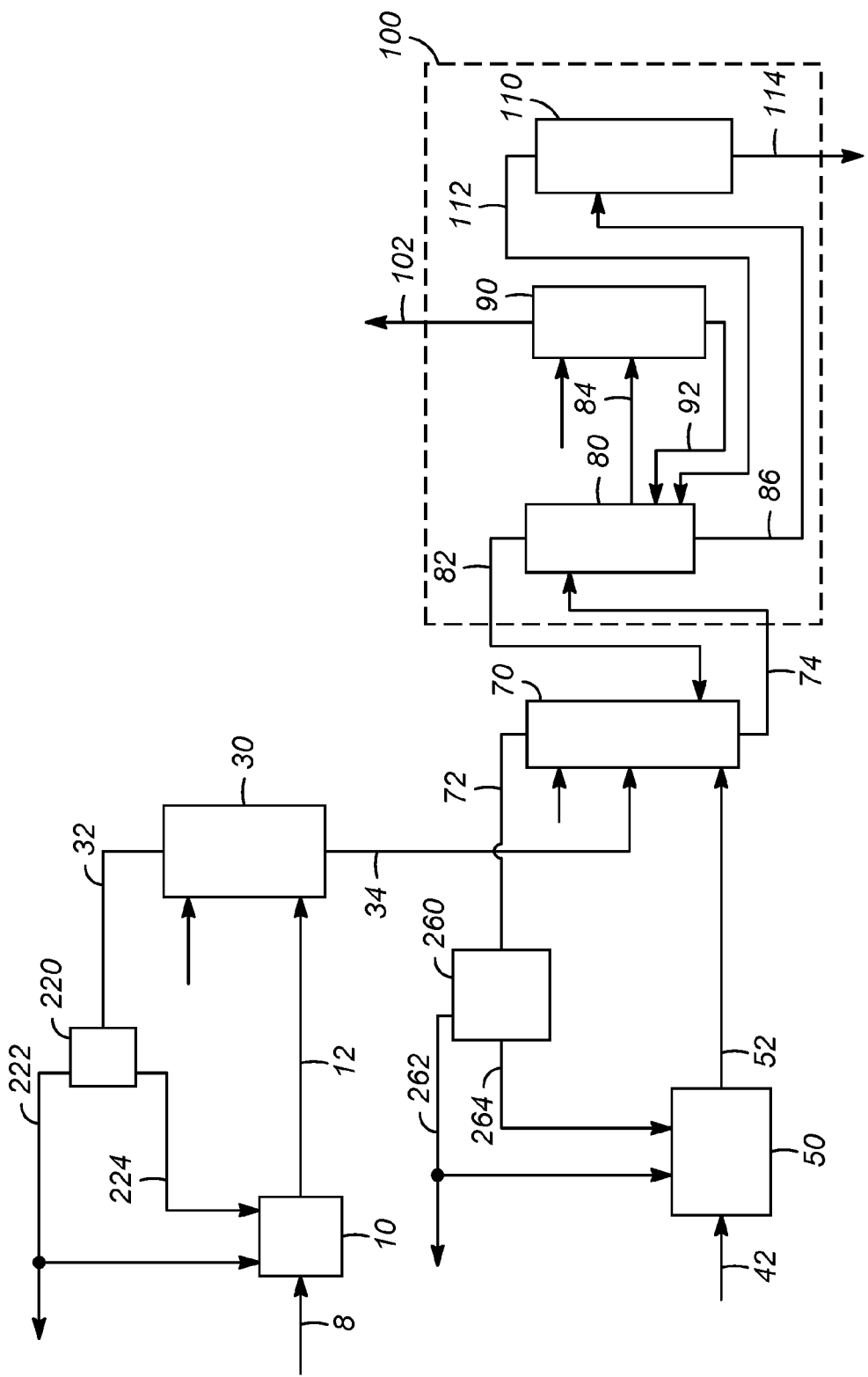
FIG. 2 is a second embodiment of the flow scheme of the present invention tying the production of butenes and butadienes together.

Turning to FIG. 2, another embodiment of the invention is shown where the first 220 and second 260 light gas separation units are located on the overhead stream 32 of the butane extraction column 30 and on the overhead stream 72 of the butene extraction column 70, respectively. In one embodiment, the first 220 and second 260 light gas separation units comprise cold-box condensing units. Butanes and butenes have moderate boiling points that are near the freezing point of water. Cooling a gas stream comprising butanes and butenes can be accomplished with a low expense cold-box technology. The gas can be first expanded to cool the gas, then passed through a heat exchanger that cools the expanded gas to a temperature below −15° C. The C4 hydrocarbons then condense while lighter gases such as hydrogen and any carbon oxides remain in the gaseous phase. The cold-box condensing units 220, 260 are operated at a temperature to sufficiently condense the C4 hydrocarbons. Different C4 hydrocarbons condense at temperatures between 1° C. and −12° C. at one atmosphere. The cold-box units 220, 260 are preferably operated at a temperature below −15° C. The light gases, including hydrogen, are readily separated from the C4 compounds at these temperatures.

Overhead stream 32 can be passed to a first light gas separation unit 220 to generate a vapor phase stream 222 comprising hydrogen, and a butene stream 224 comprising n-butene. At least a portion of streams 222 and 224 are passed to the dehydrogenation unit 10. Overhead stream 72 can be passed to a second light gas separation unit 260 to generate a vapor phase stream 262 comprising hydrogen, and a butene stream 264 comprising n-butene. At least a portion of streams 262 and 264 are passed to the oxydehydrogenation unit 50.

In another embodiment, the process also involves measuring a first parameter of the process and generating an electrical signal associated with the first parameter. The electrical signal associated with the first parameter is transmitted to a processer which generates a second electrical signal. The second electrical signal is transmitted to a component of the process to affect an adjustment of a second parameter of the process in response to the second electrical signal. The first and second parameters may be the same or different. The parameters may be operating conditions or other parameters associated with the process such as maintenance parameters, safety parameters, catalyst related parameters, equipment related parameters, and the like. In another embodiment, the process further comprises connecting, electronically, at least a first component of the process to at least a second component of the process wherein the connection incorporates at least one processor. The process may further comprise comprising sensing and collecting data regarding the process and adjusting the process in response to the sensed and collected data.

Specific Embodiments

While the following is described in conjunction with specific embodiments, it will be understood that this description is intended to illustrate and not limit the scope of the preceding description and the appended claims.

A first embodiment of the invention is a process for the recovery of butadiene, comprising passing a first feedstream comprising n-butane to a dehydrogenation unit to generate a first butene process stream comprising n-butene; passing the first n-butene process stream to a butane extraction column to generate a butane overhead stream and a first n-butene stream, wherein the butane extraction column is operated to recover the n-butenes in the first butene stream; passing the first n-butene process stream to a butene extraction column to generate an overhead stream comprising n-butene, and a bottoms stream comprising butadiene passing the overhead stream to an oxydehydrogenation unit to generate a second process stream comprising n-butene and butadiene; passing the second process stream to a butene extraction column to generate an overhead stream comprising n-butene, and a bottoms stream comprising butadiene; passing at least one feedstream derived from an FCC process or from an OTO process to the butane extraction column, to the butene extraction column, or to both the butane and butene extraction columns; and passing the bottoms stream to a butadiene recovery unit to generate a butadiene stream. An embodiment of the invention is one, any or all of prior embodiments in this paragraph up through the first embodiment in this paragraph further comprising passing a second feedstream comprising n-butene to an oxydehydrogenation unit to generate a second process stream comprising n-butene and butadiene; and passing the second process stream to the butene extraction column. An embodiment of the invention is one, any or all of prior embodiments in this paragraph up through the first embodiment in this paragraph further comprising passing the butadiene stream to a butadiene purification unit. An embodiment of the invention is one, any or all of prior embodiments in this paragraph up through the first embodiment in this paragraph further comprising passing the first butene process stream to a light gas separation unit to generate a vapor phase stream comprising hydrogen, and a liquid phase stream comprising n-butane and n-butene, wherein the light gas separation unit is a cold-box separation unit; and passing the liquid phase stream to a butane extraction column to generate a butane overhead stream and the first n-butene process stream. An embodiment of the invention is one, any or all of prior embodiments in this paragraph up through the first embodiment in this paragraph further comprising passing the butane overhead stream to the dehydrogenation unit. An embodiment of the invention is one, any or all of prior embodiments in this paragraph up through the first embodiment in this paragraph further comprising passing a portion of the vapor phase stream to the dehydrogenation unit. An embodiment of the invention is one, any or all of prior embodiments in this paragraph up through the first embodiment in this paragraph wherein the light gas separation unit is a cold-box separation unit to condense the butane and butenes, while separating hydrogen and other light gases from the first process stream. An embodiment of the invention is one, any or all of prior embodiments in this paragraph up through the first embodiment in this paragraph further comprising passing a solvent to the butane extraction column. An embodiment of the invention is one, any or all of prior embodiments in this paragraph up through the first embodiment in this paragraph wherein the solvent is selected from the group consisting of n-methyl-2-pyrrolidone (NMP), dimethylformamide (DMF), acetonitrile (ACN), and mixtures thereof. An embodiment of the invention is one, any or all of prior embodiments in this paragraph up through the first embodiment in this paragraph wherein the oxydehydrogenation unit generates an intermediate stream, further comprising passing the intermediate stream to a second light gas separation unit to generate a second light gas stream and a second intermediate stream comprising butadiene and n-butene; and passing the second intermediate stream to the butene extraction column. An embodiment of the invention is one, any or all of prior embodiments in this paragraph up through the first embodiment in this paragraph further comprising passing a solvent to the butene extraction column. An embodiment of the invention is one, any or all of prior embodiments in this paragraph up through the first embodiment in this paragraph further comprising passing steam and air to the oxydehydrogenation unit. An embodiment of the invention is one, any or all of prior embodiments in this paragraph up through the first embodiment in this paragraph wherein passing the bottoms stream to the butadiene recovery unit comprises passing the bottoms stream to a rectifying column to generate an overhead stream, an intermediate stream comprising butadiene, and a rectifying bottoms stream; passing the rectifying bottoms stream to a degassing column to generate a degassing column overhead stream an a solvent recovery bottoms stream; passing the degassing column overhead stream to the rectifying column; passing the intermediate stream to a butadiene extraction column to generate a butadiene extraction column bottoms comprising solvent and n-butene, and the butadiene stream. An embodiment of the invention is one, any or all of prior embodiments in this paragraph up through the first embodiment in this paragraph further comprising passing a solvent to the butadiene extraction column. An embodiment of the invention is one, any or all of prior embodiments in this paragraph up through the first embodiment in this paragraph further comprising measuring a first parameter of the process and generating an electrical signal associated with the parameter; transmitting the electrical signal to a processer and generating a second electrical signal; transmitting the second electrical signal to a component of the process and adjusting a second parameter of the process in response to the second electrical signal. An embodiment of the invention is one, any or all of prior embodiments in this paragraph up through the first embodiment in this paragraph further comprising connecting, electronically, at least a first component of the process to at least a second component of the process wherein the connection incorporates at least one processor. An embodiment of the invention is one, any or all of prior embodiments in this paragraph up through the first embodiment in this paragraph further comprising sensing and collecting data regarding the process and adjusting the process in response to the sensed and collected data.

A second embodiment of the invention is a process for the recovery of butadiene, comprising passing a first stream comprising n-butane to a dehydrogenation reactor to generate a second stream comprising n-butane and n-butene; passing the second stream to a light gas separation unit to generate a vapor phase comprising hydrogen, and a third stream comprising liquid n-butane and n-butene; passing the third stream to a butane extraction column to generate a fourth stream comprising n-butane and a fifth stream comprising n-butene; passing the fifth stream to a butene extraction column; passing a sixth stream comprising n-butene to an oxydehydrogenation reactor to generate a seventh stream comprising butadiene and n-butene; passing the seventh stream to a second light gas separation unit to generate a second vapor phase comprising light gases, and an eighth stream comprising butadiene and n-butene; and passing the eighth stream to the butene extraction column to generate a ninth stream comprising n-butene, and a tenth stream comprising butadiene. An embodiment of the invention is one, any or all of prior embodiments in this paragraph up through the second embodiment in this paragraph wherein the fifth stream and the eighth stream are passed to the butene extraction column at different stages. An embodiment of the invention is one, any or all of prior embodiments in this paragraph up through the second embodiment in this paragraph further comprising passing the tenth stream to a rectifying column to generate an overhead stream an intermediate stream comprising butadiene and a bottoms stream comprising solvent; and passing the intermediate stream to a butadiene extraction column to generate a butadiene product stream and a bottoms stream. An embodiment of the invention is one, any or all of prior embodiments in this paragraph up through the second embodiment in this paragraph further comprising passing the butadiene extraction column bottoms stream to the rectifying column. An embodiment of the invention is one, any or all of prior embodiments in this paragraph up through the second embodiment in this paragraph further comprising passing the rectifying column bottoms stream to a degassing column to generate a degassing column overhead and a recovered solvent bottoms stream; and passing the degassing column overhead stream to the rectifying column. An embodiment of the invention is one, any or all of prior embodiments in this paragraph up through the second embodiment in this paragraph further comprising passing steam and air to the oxydehydrogenation reactor. An embodiment of the invention is one, any or all of prior embodiments in this paragraph up through the second embodiment in this paragraph wherein the extraction columns comprise passing a solvent to the extraction column.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for the recovery of butadiene, comprising:
    passing a first feedstream comprising n-butane to a dehydrogenation unit to generate a first butene process stream comprising n-butene;
    passing the first n-butene process stream to a butane extraction column to generate a butane overhead stream and a first n-butene stream, wherein the butane extraction column is operated to recover the n-butenes in the first butene stream;
    passing the first n-butene process stream to a butene extraction column to generate an overhead stream comprising n-butene, and a bottoms stream comprising butadiene;
    passing the overhead stream to an oxydehydrogenation unit to generate a second process stream comprising n-butene and butadiene;
    passing the second process stream to a butene extraction column to generate an overhead stream comprising n-butene, and a bottoms stream comprising butadiene;
    passing at least one feedstream derived from an FCC process or from an OTO process to the butane extraction column, to the butene extraction column, or to both the butane and butene extraction columns; and
    passing the bottoms stream to a butadiene recovery unit to generate a butadiene stream.

2. The process of claim 1 further comprising:
    passing a second feedstream comprising n-butene to an oxydehydrogenation unit to generate a second process stream comprising n-butene and butadiene; and
    passing the second process stream to the butene extraction column.

3. The process of claim 1 further comprising:
    passing the first butene process stream to a light gas separation unit to generate a vapor phase stream comprising hydrogen, and a liquid phase stream comprising n-butane and n-butene; and
    passing the liquid phase stream to a butane extraction column to generate a butane overhead stream and the first n-butene process stream.

4. The process of claim 3 further comprising:
    passing the butane overhead stream to the dehydrogenation unit; and
    passing a portion of the vapor phase stream to the dehydrogenation unit.

5. The process of claim 3 wherein the light gas separation unit is a cold-box separation unit to condense the butane and butenes, while separating hydrogen and other light gases from the first process stream.

6. The process of claim 1 further comprising passing a first solvent to the butane extraction column and a second solvent to the butene extraction column wherein the first and second solvents are selected from the group consisting of n-methyl-2-pyrrolidone (NMP), dimethylformamide (DMF), acetonitrile (ACN), and mixtures thereof.

7. The process of claim 1 wherein the oxydehydrogenation unit generates an intermediate stream, further comprising:
    passing the intermediate stream to a second light gas separation unit to generate a second light gas stream and a second intermediate stream comprising butadiene and n-butene; and
    passing the second intermediate stream to the butene extraction column.

8. The process of claim 1 further comprising passing steam and air to the oxydehydrogenation unit.

9. The process of claim 1 wherein passing the bottoms stream to the butadiene recovery unit comprises:
    passing the bottoms stream to a rectifying column to generate an overhead stream, an intermediate stream comprising butadiene, and a rectifying bottoms stream;
    passing the rectifying bottoms stream to a degassing column to generate a degassing column overhead stream an a solvent recovery bottoms stream;
    passing the degassing column overhead stream to the rectifying column; and
    passing the intermediate stream to a butadiene extraction column to generate a butadiene extraction column bottoms comprising solvent and n-butene, and the butadiene stream.

10. The process of claim 9 further comprising passing a solvent to the butadiene extraction column.

11. The process of claim 1 further comprising:
    measuring a first parameter of the process and generating an electrical signal associated with the parameter;
    transmitting the electrical signal to a processer and generating a second electrical signal;
    transmitting the second electrical signal to a component of the process and adjusting a second parameter of the process in response to the second electrical signal.

12. The process of claim 1 further comprising connecting, electronically, at least a first component of the process to at least a second component of the process wherein the connection incorporates at least one processor.

13. The process of claim 1 further comprising sensing and collecting data regarding the process and adjusting the process in response to the sensed and collected data.

14. The process of claim 1 wherein the feedstream derived from a FCC process is introduced to the butane extraction column.

15. The process of claim 1 wherein the feedstream derived from an OTO process is introduced to the butene extraction column.

16. A process for the recovery of butadiene, comprising:
    passing a first feedstream comprising n-butane to a dehydrogenation unit to generate a first butene process stream comprising n-butene;
    passing the first butene process stream to a butane extraction column to generate a butane overhead stream and a first butene stream, wherein the butane extraction column is operated to recover the n-butenes in the first butene stream;

passing the butane overhead stream to a light gas separation unit to generate a vapor phase stream comprising hydrogen, and a liquid phase stream comprising n-butane;

passing at least a portion of the stream comprising hydrogen and at least a portion of the liquid phase stream to the dehydrogenation unit;

passing the first butene stream to a butene extraction column to generate an overhead stream comprising butene, and a bottoms stream comprising butadiene;

passing the overhead stream comprising butene to an oxydehydrogenation unit to generate a second process stream comprising butene and butadiene;

passing the second process stream comprising butene to the butene extraction column; and passing the bottoms stream to a butadiene recovery unit to generate a butadiene stream.

17. A process for the recovery of butadiene, comprising:

passing a first feedstream comprising n-butane to a dehydrogenation unit to generate a first butene process stream comprising n-butene;

passing the first butene process stream to a butane extraction column to generate a butane overhead stream and a first butene stream, wherein the butane extraction column is operated to recover the n-butenes in the first butene stream;

passing the first butene stream to a butene extraction column to generate an overhead stream comprising butene, and a bottoms stream comprising butadiene;

passing the overhead stream comprising butene to a light gas separation unit to generate a vapor phase stream comprising hydrogen, and a liquid phase stream comprising butene;

passing at least a portion of the stream comprising hydrogen and at least a portion of the liquid phase stream to an oxydehydrogenation unit;

passing a second feedstream comprising n-butene to the oxydehydrogenation unit to generate a second process stream comprising n-butene and butadiene;

passing the second process stream to the butene extraction column; and passing the bottoms stream comprising butadiene to a butadiene recovery unit to generate a butadiene stream.

* * * * *